United States Patent
Husemann et al.

(10) Patent No.: US 7,432,326 B2
(45) Date of Patent: Oct. 7, 2008

(54) PRESSURE-SENSITIVE ADHESIVE BASED ON ACRYLATE BLOCK COPOLYMERS

(75) Inventors: Marc Husemann, Hamburg (DE); Thilo Dollase, Hamburg (DE); Bernd Lühmann, Norferstedt (DE)

(73) Assignee: tesa Aktiengesellschaft, Hamburg (DE)

( * ) Notice: Subject to any disclaimer, the term of this patent is extended or adjusted under 35 U.S.C. 154(b) by 0 days.

(21) Appl. No.: 10/992,860

(22) Filed: Nov. 19, 2004

(65) Prior Publication Data

US 2005/0154137 A1 Jul. 14, 2005

(30) Foreign Application Priority Data

Jan. 9, 2004 (DE) .................. 10 2004 001 412

(51) Int. Cl.
*C08L 53/00* (2006.01)

(52) U.S. Cl. .................................. 525/89; 525/94

(58) Field of Classification Search .................. 525/89, 525/94

See application file for complete search history.

(56) References Cited

U.S. PATENT DOCUMENTS

| | | | | |
|---|---|---|---|---|
| 4,581,429 A | 4/1986 | Solomon et al. | ............. | 526/220 |
| 5,767,210 A | 6/1998 | Lecomte et al. | ............. | 526/166 |
| 5,789,487 A | 8/1998 | Matyjaszewski et al. | .... | 525/301 |
| 5,811,500 A | 9/1998 | Dubois et al. | ............... | 526/145 |
| 5,854,364 A | 12/1998 | Senninger et al. | ........... | 526/192 |
| 5,919,871 A | 7/1999 | Nicol et al. | .............. | 525/333.8 |
| 5,945,491 A | 8/1999 | Matyjaszewski et al. | .... | 526/111 |
| 6,114,482 A | 9/2000 | Senninger et al. | ........... | 526/172 |
| 6,479,608 B1 | 11/2002 | Nesvadba et al. | ........ | 526/328.5 |
| 6,586,491 B2 | 7/2003 | Husemann et al. | ............ | 522/35 |
| 2002/0193539 A1 | 12/2002 | Husemann et al. | .......... | 526/217 |
| 2003/0096075 A1* | 5/2003 | Dollase et al. | ............. | 428/40.1 |
| 2003/0105258 A1 | 6/2003 | Husemann et al. | .......... | 526/319 |
| 2004/0092685 A1 | 5/2004 | Husemann et al. | .......... | 526/217 |

FOREIGN PATENT DOCUMENTS

| | | |
|---|---|---|
| DE | 19949352 | 4/2000 |
| DE | 10008842 | 6/2001 |
| DE | 10030217 | 1/2002 |
| DE | 10036801 | 2/2002 |
| DE | 10149084 | 6/2003 |
| EP | 0735052 | 10/1996 |
| EP | 0824110 | 2/1998 |
| EP | 0824111 | 2/1998 |
| EP | 0826698 | 3/1998 |
| EP | 0841346 | 5/1998 |
| EP | 0850957 | 7/1998 |
| WO | WO 96/24620 | 8/1996 |
| WO | WO 98/01478 | 1/1998 |
| WO | WO 98/13392 | 4/1998 |
| WO | WO 98/44008 | 10/1998 |
| WO | WO 99/31144 | 6/1999 |

* cited by examiner

*Primary Examiner*—Jeffrey C Mullis
(74) *Attorney, Agent, or Firm*—Norris McLaughlin & Marcus PA

(57) ABSTRACT

The invention provides an acrylate-based pressure-sensitive adhesive comprising a polymer blend having (a) at least a first component $K_c$ which comprises a first acrylate block copolymer having at least two chemically distinguishable, covalently interlinked acrylate polymer blocks P, the at least two polymer blocks P independently of one another each being a homopolymer block of a first monomer or a copolymer block of a second monomer and a comonomer, and the first monomer of the homopolymer block and the second monomer of the copolymer block can be identical or different from one another, and the at least two polymer blocks P being present under application conditions in microphase-separated regions and each having a softening temperature of between −125 and +20° C., and (b) at least one second component $L_D$, which is a second acrylate block copolymer, distinguishable from component $K_c$, having at least two chemically distinguishable, covalently interlinked acrylate polymer blocks P, with the features specified under (a), or is an acrylate polymer $P_S$, which is a homopolymer of a first monomer or a copolymer of a second monomer and a comonomer, the acrylate polymer $P_S$ and the acrylate polymer blocks P having softening temperatures of between −125 and +20° C.

36 Claims, No Drawings

PRESSURE-SENSITIVE ADHESIVE BASED ON ACRYLATE BLOCK COPOLYMERS

The invention relates to a pressure-sensitive adhesive (PSA) based on an acrylate polymer blend and to self-adhesive tapes produced from it.

BACKGROUND OF THE INVENTION

Polyacrylate-based PSAs have already been known for more than 40 years. Within this period polyacrylate PSAs have proven themselves in a multiplicity of different applications, and have become established accordingly. As compared with the PSAs that are likewise widely utilized in self-adhesive tapes but are based on rubbers (e.g. natural rubber or styrene-butadiene rubber) or based on styrene block copolymers (SIS, SBS) they possess numerous advantages. These include their excellent UV and light stability, high resistance to thermooxidative ageing, custom-tailorable polarity and, typically, water-clear transparency. In polyacrylate PSAs, moreover, there is generally an inherent possibility for crosslinking of the polymer chains, a possibility which is generally exploited; as a result these PSAs even at relatively high service temperatures possess good cohesion and hence a high level of temperature stability of the bonds. A further advantage is that polyacrylate PSAs already possess pressure-sensitive tack per se, in other words without additional additives, such as tackifying resins or plasticizers, for example.

New applications, especially industrial applications, are imposing ever more extensive requirements on the performance of polyacrylate PSAs. With the systems available to date, meeting such requirements is in many cases very difficult and in others completely impossible.

Conventional approaches to controlling the properties of polyacrylate PSAs include the choice of identity and quantity of the comonomers employed, the adjustment of molar mass and molar mass distribution in the polymers, and the mode and extent of crosslinking of the polymers. The aforementioned parameters allow the profile of adhesives properties to be controlled with selectivity and precision.

It is found in this context that the comonomers available industrially which can be employed economically for polyacrylate PSAs are limited. Increasing restrictions are coming about, moreover, as a result of progressively tightened statutory regulations. Thus, for example, vinyl acetate and acrylamide have become two relatively objectionable base materials.

In order to meet the increasing requirements made of polyacrylate PSAs the more recent past has seen targeted development of polymerization processes for controlling the molecular weight distribution (DE 100 30 217; DE 100 36 801; DE 101 49 084). Polyacrylates synthesized with such polymerization processes can be utilized with advantage for applications which include pressure-sensitive adhesives that can be coated from the melt. The achievable potential for improvement, however, is limited.

Another path taken to get to improved products involves the possibility of selective synthesis of block copolymers (I. W. Hamley, The Physics of Block Copolymers, 1998, Oxford University Press, Oxford). As a result of chemical coupling of thermodynamically incompatible polymer blocks, such block copolymers exhibit microphase separation: that is, thermodynamically compatible polymer blocks associate while thermodynamically incompatible polymer blocks segregate into spatially separate regions, but without macroscopic phase separation. The result, depending on composition, are phases of different structure. Block copolymers utilized at present in PSAs typically possess two or more polymer blocks of high softening temperature (also referred to below as hard blocks; realized by means of a correspondingly high glass transition temperature or a correspondingly high crystallite melting temperature) and at least one block of low softening temperature (also referred to below as soft block). The composition here has been chosen so that the phase formed by the soft blocks forms a continuous matrix within the PSA, thereby endowing the system with the possibility of PSA properties. The polymer blocks which soften at high temperature associate or segregate to form phase regions (domains) which are typically approximately globular, which are present in dispersion in the continuous matrix of the soft phase and which below their glass transition temperature or crystallite melting temperature act as physical crosslinking points (G. Holden, N. R. Legge, R. P. Quirk, H. E. Schroeder (eds.), Thermoplastic Elastomers, 2nd Ed., 1996, C. Hanser Verlag, Munich). Advantages of PSAs based on such block copolymers include, for example, the possibility of realizing very high shear strengths.

A third way to improve conventional acrylate PSAs leads via polymer blends (DE 100 08 842.2). Polymer blends frequently allow the positive properties of the individual components to be combined with one another and in some cases allow synergistic effects to be achieved to boot.

A disadvantage of the aforementioned block copolymers is that in the case of their solvent-free processing the processing temperatures are typically situated well above the softening temperature of the hard block domains (in the case of hard blocks which solidify glassily the required coating temperatures are above—in some cases at least about 30K to 50K or further above—the glass transition temperature (Tg) of the hard block domains) in order for the melt viscosity and/or elasticity to be sufficiently low.

A further disadvantage is the fact that the thermal load-bearing capacity of PSAs based on abovementioned block copolymers, crosslinked physically by way of the hard block domains, is markedly limited as a result of the softening of the hard block domains at high temperatures.

A disadvantage of the known block copolymers comprising hard and soft blocks is the fact, moreover, that the only phase structures obtainable with them that can be used for PSAs are those wherein the hard block phase is dispersed in the form of approximately globular associations in the continuous soft phase of the polymer block of low softening temperature. Phase structures comprising prolate, i.e. uniaxially elongated (e.g. rodlet-shaped), oblate, i.e. biaxially elongated (e.g. layer-shaped) or three-dimensionally disposed associations of the hard phase, which are typically formed at relatively high hard block concentrations, are unsuitable for the realization of PSAs, since such systems lack the sufficiently high pliability and/or lack a sufficiently low deformation modulus and so do not meet, for example, the Dahlquist criterion important for pressure-sensitive tack. The wide diversity of phase structures available for block copolymers (see e.g. H. G. Elias in "Makromoleküle"; Wiley-VCH, 6th Edition 2001, Volume 2, section 8.5.2 or I. W. Hamley, The Physics of Block Copolymers, 1998, Oxford University Press, Oxford) hence remains closed for PSAs.

A further disadvantage of known block copolymers is that in order to obtain physical crosslinking and hence in order to realize sufficient cohesion there must be at least two spatially separated polymer blocks of high softening temperature. Diblock copolymers consisting of only one hard block and one soft block are therefore of only limited suitability as a sole polymer component for use in PSAs, especially if high shear strengths are called for.

PSAs known correspondingly are thus severely restricted in their structure, and control possibilities for PSAs are limited accordingly.

The invention is based on the object of providing polymer blends based on acrylate-containing block copolymers which are suitable for use in PSAs and which overcome the above-mentioned disadvantages of known acrylate components. The acrylate-containing components ought to exhibit microphase separation and ought in particular to make the overall phase structures that are possible for block copolymers available for PSAs, thereby permitting a significant expansion of the presently accessible performance spectrum of PSAs.

SUMMARY OF THE INVENTION

The pressure-sensitive adhesive of the invention comprises a polymer blend having (a) at least a first component $K_c$ which comprises a first acrylate block copolymer having at least two chemically distinguishable, covalently interlinked acrylate polymer blocks P, the at least two polymer blocks P independently of one another each being a homopolymer block of a first monomer or a copolymer block of a second monomer and a comonomer, and it being possible for the first monomer of the homopolymer block and the second monomer of the copolymer block to be identical to or different from one another, the at least two polymer blocks P being present under application conditions in microphase-separated regions and each having a softening temperature of between −125 and +20° C., and (b) at least one second component $L_D$, which is a second acrylate block copolymer, distinguishable from component $K_c$, having at least two chemically distinguishable, covalently interlinked acrylate polymer blocks P, with the features specified under (a), or is an acrylate polymer $P_S$, which is a homopolymer of a first monomer or a copolymer of a second monomer and a comonomer, the acrylate polymer $P_S$ and the acrylate polymer blocks P having softening temperatures of between −125 and +20° C.

DETAILED DESCRIPTION

The invention accordingly provides a pressure-sensitive adhesive based on a polymer blend composed of at least two acrylate components $K_c$ and $L_D$ which may both (chemically distinguishable from one another) be acrylate block copolymers having in principle the same general structure. Alternatively the second component can also be an acrylate homopolymer or copolymer, corresponding to an acrylate block copolymer with only one polymer block.

The individual components $K_c$ and $L_D$ and/or the immiscible or incompletely miscible polymer blocks of the individual components each have a softening temperature of between −125 and +20° C., in particular in the range between −100° C. and +20° C., preferably between −80° C. and +20° C. By softening temperature here is meant, in the context of the present invention, a glass transition temperature for amorphous systems and a melting temperature in the case of semi-crystalline polymers. The temperatures given here are in accordance with those obtained from quasi-steady-state experiments, such as by means of differential scanning calorimetry (DSC), for example.

A significant advantage of polymer blends of the invention includes the control over the adhesive properties by way of the possible orientation of anisotropic microphase-separated regions. In particular it is possible here in principle to establish all advantageous domain structures of the microseparated phases, such as elongated, microphase-separated regions, in the form for example of prolate, uniaxially elongated (e.g. rodlet-shaped) structural elements, oblate, biaxially elongated (e.g. layer-shaped) structural elements, three-dimensionally cocontinuous microphase-separated regions, or a continuous matrix with regions dispersed therein.

The polymer blends of component $K_c$ and $L_D$ are composed in one preferred embodiment of from 5 to 95% of $K_c$ and from 95 to 5% of $L_D$: that is, both components have a mass fraction in the polymer blend of at least 5%. The composition of the polymer blends is chosen such that under application conditions a microphase-separated system is present and that at least one phase of component $K_c$ is miscible with one phase of component $L_D$.

Additionally, in a further embodiment, it is also possible for two or more components $K_c$ to be blended with two or more components $L_D$.

In one advantageous embodiment the second component $L_D$ in the form of the acrylate polymer $P_S$ is present as a homopolymer P(A) of a first monomer A or as a copolymer of the monomer A and the copolymer C. Preferred monomers A and C are elucidated later on below.

Alternatively the second component $L_D$—just like the first component $K_c$—can be an acrylate block comonomer. The acrylate block copolymer of the first component $K_c$ and/or the acrylate block copolymer of the second component $L_D$ preferably has a structure in accordance with the general stoichiometric formula (I)

$$[P1_i\text{-}P2_j]_k \qquad (I)$$

in which P1 is a first polymer block of at least one first monomer and P2 is a second polymer block of at least one second monomer, the indices i and j indicating the number of the first and second polymer blocks, respectively, within the structural unit $[P1_i\text{-}P2_j]$ and k indicating the number of the structural unit within the acrylate block copolymer of formula (I), i, j, k being a positive integer i, j, k>0. P1 and P2 can here in turn each be homopolymer or copolymer blocks.

Utilized with particular preference in accordance with the invention for use in PSAs in the components $K_D$ and/or $L_D$ are diblock copolymers of formula (I) with i=j=k=1, and hence the block copolymers simplest in construction and most easy to synthesize, with the structure P1-P2, and also triblock copolymers of formula (I) with i+j=3 (i, j>0) and k=1, with the structures P1-P2-P1 or P2-P1-P2. In these copolymers it is possible in each case for the first polymer block P1 to be a polymer P(A) of the monomer A or a copolymer P(A/C) of the monomers A and C and for the second polymer block P2 to be a polymer P(B) of the monomer B or a copolymer P(B/D) of the monomers B and D. A and B here stand for one or more monomers of type A and respectively for one or more monomers of type B (for detailed description see below), which can be utilized for preparing the respective polymer block. With particular preference here, in the case of the diblock copolymers, the mass fraction of the first polymer block P1 in the macromolecule is in the range from 20 to 95%, preferably from 25 to 80%, and, in the case of the triblock copolymers, it is in the range from 5 to 95%, preferably from 10 to 90%. The same applies respectively to the second polymer block P2. Within these ranges the presence of the desired, above-mentioned domain structures of the microphase-separated regions is ensured. Preferred diblock and triblock copolymers are elucidated later on below in connection with the individual components $L_D$ and $K_c$.

Likewise embraced by the invention as block copolymers for the components $K_D$ and/or $L_D$ are linear and star-shaped multiblock copolymers of the general formulae $$[P1\text{-}P2\text{-}P3\text{-}\ldots\text{-}Pm], \tag{II}$$

in which P1 to Pm are m distinguishable polymer blocks with m>3 and, respectively, $$\{P1_\delta\text{-}P2_\delta\text{-}P3_\delta\text{-}\ldots\text{-}Pn_\delta\}_xX, \tag{III}$$

in which P1 to Pn are n distinguishable polymer blocks, with n>1, X is a polyfunctional crosslinking region to which x polymer arms, with x>2, are chemically attached, and the serial number δ indicates the number of a polymer block P within the respective polymer arm, with δ=1 or 2. In both cases the polymer blocks P can independently of one another each be a homopolymer block P(E) of the monomer E or a copolymer block P(E/F) of the monomer E and the comonomer F. Preferred multiblock copolymers are elucidated later on below in connection with the individual components $L_D$ and $K_c$.

Monomers which can be used for monomer types A, B and E and also for the comonomers C, D and F are likewise elucidated later on below. For the comonomers C, D and F which can be used in the copolymer blocks P(A/C), P(B/D) and P(E/F) it is the case, in a particularly preferred version, that these comonomers have a functional and/or polar group which itself is substantially non-polymerizable but is suitable for entering into non-covalent interactions with further polymer macromolecules, in particular hydrogen bonds and/or dipole-dipole interactions. These interactions have the effect, advantageously, of raising the cohesion of the block copolymer. The comonomers C, D and/or F are preferably represented with a mass fraction of from 0.1 to 50%, in particular from 0.5 to 30%, preferably from 1 to 20%, within the corresponding copolymer blocks.

In one preferred version of the invention the components $K_c$ and $L_D$ meet one or more of the following criteria:
a molar mass $M_n$ of below 10 000 000 g/mol, preferably a molar mass of between 30 000 and 1 000 000 g/mol,
a polydispersity $D=M_w/M_n$ of less than 5, preferably less than 3,
one or more grafted-on side chains.

The invention further provides for the use of the pressure-sensitive adhesive of the invention for self-adhesive tapes, the pressure-sensitive adhesive being applied to one or both sides of a backing material in tape form. It can also be employed as a straight pressure-sensitive adhesive in adhesive transfer tapes. The invention additionally provides an adhesive tape which comprises a backing material in tape form and a pressure-sensitive adhesive in accordance with the invention applied to one or both sides of the backing material over at least part of its area.

Component $L_D$

In one advantageous version the pressure-sensitive adhesive of the invention is based on a polymer blend composed of two components $K_c$ and $L_2$, in which the first component $K_c$ is characterized by an acrylate block copolymer that contains a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_1$ is composed of a polymer P(A) or P(A/C) which has a softening temperature in the range between −125 and +20° C., preferably between −100 and +20° C., P(A) being a polymer of at least one monomer of type A and P(A/C) being a copolymer of in each case at least one monomer of type A and type C.

By softening temperature here is meant a glass transition temperature for amorphous systems and a melting temperature in the case of semi-crystalline polymers. The temperatures indicated here correspond to those obtained from quasistatic experiments, such as by means of DSC, for example.

The invention further provides a pressure-sensitive adhesive based on a polymer blend composed of two components $K_c$ and $L_2$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and of a component $L_2$ composed of a diblock copolymer comprising two interconnected polymer blocks of the general type P(A)-P(B/D), in which each block copolymer is composed of a first polymer block P(A) and a copolymer block P(B/D) attached thereto, where P(A) represents a polymer obtained by polymerizing at least one monomer of type A, P(A) having a softening temperature of between −125 and +20° C., preferably between −100 and +20° C., more preferably between −80 and +20° C., P(B/D) represents a copolymer obtained by copolymerizing at least one monomer of type B and at least one monomer of type D, P(B/D) having a softening temperature of between −125 and +20° C., preferably between −100 and +20° C., more preferably between −80 and +20° C. Monomers of type D possess at least one functional group which behaves substantially inertly in a free-radical copolymerization reaction, and serves in particular for raising the cohesion of the block copolymer, and polymer blocks P(A) and P(B/D) are in microphase-separated form under application conditions, and so the polymer blocks P(A) and P(B/D) are not completely (homogeneously) miscible under application conditions.

The invention further provides a pressure-sensitive adhesive based on a polymer blend composed of two components $K_c$ and $L_3$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_3$ is composed of a diblock copolymer of the general type P(A/C)-P(B/D) or of the general type P(A)-P(B), where P(A) and P(B) each represent a polymer block obtained by polymerizing at least one monomer of type A or type B, respectively, P(A) and P(B) having a softening temperature of between −125 and +20° C., preferably between −100 and +20° C., more preferably between −80 and +20° C.

P(A/C) and P(B/D) each represent a copolymer block obtained by copolymerizing at least one monomer of type A and at least one monomer of type C or at least one monomer of type B and at least one of type D, respectively, P(A/C) and P(B/D) having a softening temperature of between −125 and +20° C., preferably between −100 and +20° C., more preferably between −80 and +20° C. Monomers of type C and D possess at least one functional group which behaves substantially inertly in a free-radical polymerization reaction, and which serves in particular for raising the cohesion of the block copolymer.

Polymer blocks P(A) and P(B) or polymer blocks P(A/C) and P(B/D) are in microphase-separated form under application conditions, and such polymer blocks are therefore not completely (homogeneously) miscible under application conditions.

A cohesion-raising effect of the copolymer block P(B/D) can be brought about advantageously by means of bonds between the individual block copolymer macromolecules P(A)-P(B/D), the functional groups of the comonomers of type D of one block copolymer macromolecule interacting with at least one further block copolymer macromolecule. In a particularly advantageous way the functional group of the comonomers of type D brings about the desired raising of cohesion by means of dipole-dipole interactions and/or hydrogen bonds. A particularly preferred functional group of the comonomers of type D is a carboxylic acid group or a hydroxyl group. In the same way as for monomers D this also applies to monomers C in copolymer blocks P(A/C).

Monomers of type A for the polymer block P(A) are selected such that the resultant polymer blocks P(A) are capable of forming a two-phase microphase-separated structure with the copolymer blocks P(B/D) or P(B). The fraction of the polymer blocks P(B/D) or P(B) is preferably between about 20 and 95% by weight, more preferably between 25 and 80% by weight of the entire block copolymer, so that polymer blocks P(B/D) or P(B) are able to form elongated, microphase-separated regions (domains), in the form for example of prolate, i.e. uniaxially elongated (e.g. rodlet-shaped) structural elements, oblate, i.e. biaxially elongated (e.g. layer-shaped) structural elements, three-dimensionally cocontinuous microphase-separated regions or a continuous matrix with regions of the polymer blocks P(A) dispersed therein.

Additionally the weight fraction of the comonomers of type C in the copolymer block P(A/C) in relation to the weight fraction of the monomers of type A is between 0.1 and 50%, preferably between 0.5 and 30%, more preferably between 1 and 20%. The same applies to comonomers of type D in the copolymer block P(B/D) in relation to the weight fraction of the monomers of type B.

The invention further provides a pressure-sensitive adhesive based on a polymer blend composed of two components $K_c$ and $L_4$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_4$ comprises three interconnected polymer blocks based on the general type P(A)-P(B/D)-P(A), in which each block copolymer is composed of a central copolymer block P(B/D) and two polymer blocks P(A) attached thereto, where P(B/D) represents a copolymer obtained by copolymerizing at least one monomer of type B and at least one monomer of type D, P(B/D) having a softening temperature of between −125 and +20° C., preferably between −100 and +20° C., more preferably between −80 and +20° C., and comonomers of type D possess at least one functional group which behaves substantially inertly in a free-radical polymerization reaction, and which serves in particular for raising the cohesion of the block copolymer, P(A) represents a polymer block obtained by polymerizing at least one monomer of type A, P(A) having a softening temperature of between −125 and +20° C., preferably between −100 and +20° C., more preferably between −80 and +20° C., and polymer blocks P(A) and P(B/D) are in microphase-separated form under application conditions, and so the polymer blocks P(A) and the polymer blocks P(B/D) are not completely (homogeneously) miscible under application conditions.

The invention further provides a pressure-sensitive adhesive based on a polymer blend composed of two components $K_c$ and $L_5$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_5$ corresponds to the general type P(B/D)-P(A)-P(B/D), in which each block copolymer is composed of a central polymer block P(A) and two polymer blocks P(B/D) attached to it on either side, characterized in that P(B/D) represents a copolymer obtained by copolymerizing at least one monomer of type B and at least one monomer of type D, P(B/D) having a softening temperature of between −125 and +20° C., preferably between −100 and +20° C., more preferably between −80 and +20° C., and monomers D possess at least one functional group which behaves substantially inertly in a free-radical polymerization reaction, and which serves in particular for raising the cohesion of the block copolymer, P(A) identifies a polymer obtained by polymerizing at least one monomer of type A, P(A) having a softening temperature of between −125 and +20° C., preferably between −100 and +20° C., more preferably between −80 and +20° C., and polymer blocks P(A) and polymer blocks P(B/D) are in microphase-separated form, and so blocks P(B/D) and P(A) are not completely miscible under application conditions.

The invention further provides a pressure-sensitive adhesive based on a polymer blend composed of two components $K_c$ and $L_6$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_6$ corresponds to the general type P(B/D)-P(A/C)-P(B/D), in which each block copolymer is composed of a central polymer block P(A/C) and two polymer blocks P(B/D) attached to it on either side, characterized in that P(B/D) and P(A/C) each represent a copolymer block obtained by copolymerizing at least one monomer of type B and at least one monomer of type D or at least one monomer of type A and at least one monomer of type C, respectively, P(B/D) and P(A/C) having a softening temperature of between −125 and +20° C., preferably between −100 and +20° C., more preferably between −80 and +20° C., and monomers C and D possess at least one functional group which behave substantially inertly in a free-radical polymerization reaction, and which serves in particular for raising the cohesion of the block copolymer, polymer blocks P(A/C) and polymer blocks P(B/D) are in microphase-separated form, and so blocks P(B/D) and P(A/C) are not completely miscible under application conditions.

The invention further provides a pressure-sensitive adhesive based on a polymer blend composed of two components $K_c$ and $L_7$, in which the first component $K_c$ comprises a combination of at least two chemically interlinked polymer blocks P1 and P2 which under application conditions are in microphase-separated form, there being at least two microphases, which have softening temperatures in the range between −125 and +20° C., preferably between −100 and +20° C., more preferably between −80 and +20° C., and component $L_7$ is composed of a linear or star-shaped multi-block copolymer whose structure is preferably as follows:

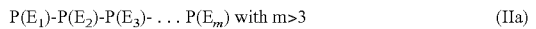  (IIa)

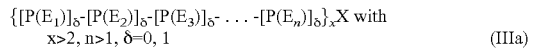  (IIIa)

where
(IIa) identifies a linear multiblock copolymer composed of n polymer blocks P(A),
(IIIa) identifies a star-shaped multiblock copolymer comprising a polyfunctional cross-linking region X, in which x polymer arms are joined to one another chemically and each polymer arm is composed of at least one polymer block P(E). Serial number δ indicates that the x polymer arms joined to one another by chemical bonding in the polyfunctional crosslinking region can each have a different number of polymer blocks P(E),
P(E) can be substituted in each case by P(E/F), and P(E) represent polymer blocks obtained by polymerizing at least one monomer of type E, and P(E/F) represent copolymer blocks obtained by copolymerizing at least one monomer of type E and at least one monomer of type F,
the individual P(E) and P(E/F) have a softening temperature of between −125 and +20° C., preferably between −100 and +20° C., more preferably between −80 and +20° C., and monomers of type F possess at least one functional group which behaves substantially inertly in a free-radical copolymerization reaction, and which serves in particular for raising the cohesion of the block copolymer,
polymers are in microphase-separated form under application conditions, and so individual polymer blocks are not completely (homogeneously) miscible under application conditions, and
at least one polymer block P(E) or P(E/F) is miscible with P(A).

Component $K_c$

Systems of component $K_c$ can be described generally by the stoichiometric formula $[P(Y)_i P(Y')_j]_k$ (III). As component $K_c$ use is made in one particularly preferred version of diblock copolymers of formula (III) with i=j=k=1 and hence the most simply constructed block copolymers and those most simple to synthesize, and triblock copolymers of formula (III) with i+j=3 (i, j>0), k=1.

Block P(Y) is advantageously constructed from at least one monomer of type A; block P(Y') represents alternatively a polymer block consisting of at least one monomer of type A or a copolymer block consisting of at least one monomer of type A and at least one monomer of type C (for detailed description see above).

Possible for use with particular preference in accordance with the invention for component $K_1$ are block copolymers P(A)-P(B), composed of two interconnected polymer blocks P(A) and P(B), where
P(A) represents a polymer obtained by polymerizing at least one monomer of type A, P(A) having a softening temperature of between −125 and +20° C., preferably between −100 and +20° C., more preferably between −80 and +20° C.
P(B) represents a polymer obtained by polymerizing at least one monomer of type B, P(B) having a softening temperature of between −125 and +20° C., preferably between −100 and +20° C., more preferably between −80 and +20° C.
Polymer blocks P(A) and P(B) are in microphase-separated form under application conditions, and so the polymer blocks P(A) and P(B) are not completely (homogeneously) miscible under application conditions.

Particularly advantageous for use are components $K_2$ composed of block copolymers comprising two interconnected polymer blocks of the general type P(A)-P(B/D), in which each block copolymer is composed of a first polymer block P(A) and a copolymer block P(B/D) attached thereto, where
P(A) represents a polymer obtained by polymerizing at least one monomer of type A, P(A) having a softening temperature of between −125 and +20° C., preferably between −100 and +20° C., more preferably between −80 and +20° C.,
P(B/D) represents a copolymer obtained by copolymerizing at least one monomer of type B, and at least one monomer of type D, P(B/D) having a softening temperature of between −125 and +20° C., preferably between −100 and +20° C., more preferably between −80 and +20° C., and monomers of type D possess at least one functional group which behaves substantially inertly in a free-radical copolymerization reaction, and which serves in particular for raising the cohesion of the block copolymer, and
polymer blocks P(A) and P(B/D) are in microphase-separated form under application conditions, and so the polymer blocks P(A) and P(B/D) are not completely (homogeneously) miscible under application conditions.

The cohesion-raising effect of the copolymer block P(B/D) can be brought about advantageously by means of bonds between the individual block copolymer macromolecules P(A)-P(B/D), the functional groups of the comonomer of type D of one block copolymer macromolecule interacting with at least one further block copolymer macromolecule. In a particularly advantageous way the functional group of the comonomers of type D brings about the desired raising of cohesion by means of dipole-dipole interactions and/or hydrogen bonds. A particularly preferred functional group of the comonomers of type D is a carboxylic acid group or a hydroxyl group.

Monomers of type A for the polymer block P(A) are selected such that the resultant polymer blocks P(A) are capable of forming a two-phase microphase-separated structure with the copolymer blocks P(B/D). The fraction of the polymer blocks P(B/D) is preferably between about 20 and 95% by weight, more preferably between 25 and 80% by weight of the entire block copolymer, so that polymer blocks P(B/D) are able to form elongated microphase-separated regions (domains), in the form for example of prolate, i.e. uniaxially elongated (e.g. rodlet-shaped), oblate, i.e. biaxially elongated (e.g. layer-shaped) structural elements, three-dimensionally co-continuous microphase-separated regions or a continuous matrix with regions of the polymer blocks P(A) dispersed therein.

Additionally the weight fraction of the comonomers of type D in the copolymer block P(B/D) in relation to the weight fraction of the monomers of type B is between 0.1 and 50%, preferably between 0.5 and 30%, more preferably between 1 and 20%.

Additionally use is made very advantageously for component $K_3$ of block copolymers of the general type P(A/C)-P(B/D), where P(A/C) and P(B/D) each represent a copolymer block obtained by copolymerizing at least one monomer of type A and at least one monomer of type C and at least one monomer of type B and at least one monomer of type D, respectively, P(A/C) and P(B/D) having a softening temperature of between −125 and +20° C., preferably between −100 and +20° C., more preferably between −80 and +20° C., and monomers of type C and D possess at least one functional group which behaves substantially inertly in a free-radical copolymerization reaction and serves in particular for raising the cohesion of the block copolymer.

Polymer blocks P(A/C) and P(B/D) are in microphase-separated form under application conditions, and such polymer blocks are therefore not completely (homogeneously) miscible under application conditions.

The mass fraction of the polymer blocks P(B/D) is preferably between about 20 and 95% by weight, more preferably between 25 and 80% by weight of the entire block copolymer, so that polymer blocks P(B/D) are able to form elongated microphase-separated regions, in the form for example of prolate (e.g. rodlet-shaped) or oblate (e.g. area-shaped) structural elements, three-dimensional co-continuous microphase-separated regions or a continuous matrix with regions of the polymer blocks P(A/C) dispersed therein.

Additionally the weight fraction of the comonomers of type D in the copolymer block P(B/D) in relation to the weight fraction of the comonomers of type B in the copolymer block P(B/D) is between 0.1 and 50%, preferably between 0.5 and 30%, more preferably between 1 and 20%. The same applies to the weight fraction of the comonomers of type C in the copolymer block P(A/C) in relation to the weight fraction of the comonomers of type A in the copolymer block P(A/C).

Block copolymers which can be used with advantage as component $K_4$ further include those of general structure Z-P(A)-P(B)-Z', Z-P(A/C)-P(B)-Z', Z-P(A/C)-P(B/D)-Z' and Z-P(A)-P(B/D)-Z', where Z and Z' can comprise further polymer blocks or else functional groups and where Z and Z' may be identical or different.

Block copolymers which are used with particular preference as component $K_5$ are those comprising a unit of three interconnected polymer blocks of type P(A)-P(B)-P(A'), it being possible for P(A) to be substituted by P(A/C) and/or for P(B) to be substituted by P(B/D) and/or for P(A') to be substituted by P(A'/C'). P(A), P(B) and P(A') identify polymer blocks obtained by polymerizing at least one monomer of type A, B or A', respectively. P(A/C), P(B/D) and P(A'/C') identify copolymer blocks obtained by copolymerizing at least one monomer of type A and at least one monomer of type C or at least one monomer of type B and one monomer of type D or at least one monomer of type A' and one monomer of type C', respectively.

Structurally possible in accordance with the invention are not only symmetrical but also asymmetrical constructions of aforementioned block copolymers, in respect both of geometric parameters (e.g. block lengths and block length distribution, and block molar mass distribution) but also of the chemical structure of the polymer blocks. In the descriptions which follow it is assumed that both kinds of polymers, both symmetric and asymmetric, can be used in accordance with the invention. In order to keep the description readable the possibility of molecular asymmetry is not taken into account explicitly in every case.

Component $K_5$ is particularly advantageous in the following version. System $K_5(a)$ comprises three interconnected polymer blocks based on the general type P(A)-P(B/D)-P(A), in which each block copolymer is composed of a central copolymer block P(B/D) and two polymer blocks P(A) attached to it, where P(B/D) represents a copolymer obtained by copolymerizing at least one monomer of type B and at least one monomer of type D, P(B/D) having a softening temperature of between −125 and +20° C., preferably between −100 and +20° C., more preferably between −80 and +20° C., comonomers of type D possessing at least one functional group which behaves substantially inertly in a free-radical polymerization reaction, and which serves in particular for raising the cohesion of the block copolymer, P(A) represents a polymer block obtained by polymerizing at least one monomer of type A, P(A) having a softening temperature of between −125 and +20° C., preferably between −100 and +20° C., more preferably between −80 and +20° C., and Polymer blocks P(A) and P(B/D) are in microphase-separated form under application conditions, and so the polymer blocks P(A) and the polymer blocks P(B/D) are not completely (homogeneously) miscible under application conditions.

The cohesion-raising effect of the copolymer block P(B/D) can be brought about advantageously by means of bonds between the individual block copolymer macromolecules P(A)-P(B/D)-P(A), the functional groups of the comonomer of type D of one block copolymer macromolecule interacting with at least one further block copolymer macromolecule. In a particularly advantageous way the functional group of the comonomers of type D brings about the desired raising of cohesion by means of dipole-dipole interactions and/or hydrogen bonds. A particularly preferred functional group of the monomers of type D is a carboxylic acid group or a hydroxyl group.

Monomers of type A for the polymer blocks P(A) are selected such that the resultant polymer blocks P(A) are capable of forming a two-phase microphase-separated structure with the copolymer blocks P(B/D). The mass fraction of the polymer blocks P(A) is preferably between 5 and 95% by weight, more preferably between 10 and 90% by weight of the overall block copolymer.

It is further the case for the polymer block P(B/D) that the weight fraction of the monomers of type D in relation to the weight fraction of the monomers of type B is between 0.1 and 50%, preferably between 0.5 and 30%, more preferably between 1 and 20%.

In a further particularly advantageous version, $K_5(b)$ is constructed as a block copolymer of the general type P(B/D)-P(A)-P(B/D), the block copolymer being composed of a central polymer block P(A) and two polymer blocks P(B/D) attached to it on either side, characterized in that P(B/D) represents a copolymer obtained by copolymerizing at least one monomer of type B and at least one monomer of type D, P(B/D) having a softening temperature of between −125 and +20° C., preferably between −100 and +20° C., more preferably between −80 and +20° C., the monomer D possessing at least one functional group which behaves substantially inertly in a free-radical polymerization reaction, and which serves in particular for raising the cohesion of the block copolymer, P(A) characterizes a polymer obtained by polymerizing at least one monomer of type A, P(A) having a softening temperature of between −125 and +20° C., preferably between −100 and +20° C., more preferably between −80 and +20° C., and Polymer blocks P(A) and polymer blocks P(B/D) are in microphase-separated form, and so blocks P(B/D) and P(A) are not completely miscible under application conditions.

The monomers of type D preferably include at least one functional group which behaves very substantially inertly in a free-radical polymerization reaction and which serves in particular for raising the cohesion of the block copolymer, in particular by means of bonds between the individual block copolymer macromolecules, the functional group of component D of one block copolymer macromolecule interacting with at least one further block copolymer macromolecule.

Preferably the mass fraction of the polymer blocks P(A) is between 5 and 95% by weight, in particular between 10 and 90% by weight of the overall block copolymer.

Additionally the weight fraction of the comonomers of type D in the copolymer block P(B/D) in relation to the weight fraction of the comonomers of type B in the copolymer block P(B/D) is between 0.1 and 50%, preferably between 0.5 and 30%, more preferably between 1 and 20%.

In a further particularly advantageous version, $K_5(c)$ is constructed as a block copolymer of the general type P(B/D)-P(A/C)-P(B/D), the block copolymer being composed of a central polymer block P(A/C) and two polymer blocks P(B/D) attached to it on either side, characterized in that P(B/D) and P(A/C) each represent a copolymer block obtained by copolymerizing at least one monomer of type B and at least one monomer of type D or at least one monomer of type A and at least one monomer of type C, P(B/D) and P(A/C) having a softening temperature of between −125 and +20° C., preferably between −100 and +20° C., more preferably between −80 and +20° C., the monomers C and D possessing at least one functional group which behaves substantially inertly in a free-radical polymerization reaction, and which serves in particular for raising the cohesion of the block copolymer, polymer blocks P(A/C) and polymer blocks P(B/D) are in microphase-separated form, and so blocks P(A/C) and P(B/D) are not completely miscible under application conditions.

The monomers of type C and D preferably include at least one functional group which behaves very substantially inertly in a free-radical polymerization reaction and which serves in particular for raising the cohesion of the block copolymer, in particular by means of bonds between the individual block copolymer macromolecules, the functional group of components C and D of one block copolymer macromolecule interacting with at least one further block copolymer macromolecule.

Preferably the mass fraction of the polymer blocks P(A/C) is between 5 and 95% by weight, in particular between 10 and 90% by weight of the overall block copolymer.

Additionally the weight fraction of the comonomers of type D in the copolymer block P(B/D) in relation to the weight fraction of the comonomers of type B is between 0.1 and 50%, preferably between 0.5 and 30%, more preferably between 1 and 20%. The same applies to the ratio of the weight fractions of the comonomers C and A in the copolymer block P(A/C).

Further advantageous and part of this invention are compounds of the general structure Z-P(A)-P(B)-P(A')-Z', it being possible for Z and Z' to comprise further polymer blocks or else functional groups and for Z and Z' to be identical or different. P(A), P(B) and P(A') can also be in the form, optionally and independently of one another, of copolymer blocks P(A/C), P(B/D) and P(A'/C'), respectively. In specific cases it is possible for individual blocks to be omitted.

Additionally use is made, as being particularly advantageous, of component $K_6$ composed of linear or star-shaped multiblock copolymers whose structure is preferably as follows:

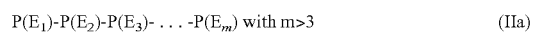

$P(E_1)\text{-}P(E_2)\text{-}P(E_3)\text{-}\ldots\text{-}P(E_m)$ with m>3     (IIa)

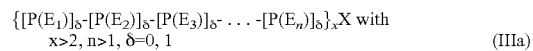

$\{[P(E_1)]_\delta\text{-}[P(E_2)]_\delta\text{-}[P(E_3)]_\delta\text{-}\ldots\text{-}[P(E_n)]_\delta\}_x X$ with x>2, n>1, δ=0, 1     (IIIa)

where
(IIa) identifies a linear multiblock copolymer composed of n polymer blocks P(A),
(IIIa) identifies a star-shaped multiblock copolymer comprising a polyfunctional cross-linking region X, in which x polymer arms are joined to one another chemically and each polymer arm is composed of at least one polymer block P(E), and serial number δ indicates that the x polymer arms joined to one another by chemical bonding in the polyfunctional crosslinking region can each have a different number of polymer blocks P(E),
P(E) can be substituted in each case by P(E/F), and P(E) represent polymer blocks obtained by polymerizing at least one monomer of type E, and P(E/F) represent copolymer blocks obtained by copolymerizing at least one monomer of type E and at least one monomer of type F,
the individual P(E) or P(E/F) have a softening temperature of between −125 and +20° C., preferably between −100 and +20° C., more preferably between −80 and +20° C., and monomers of type F possess at least one functional group which behaves substantially inertly in a free-radical copolymerization reaction and which serves in particular for raising the cohesion of the block copolymer,
polymers are in microphase-separated form under application conditions, and so individual polymer blocks are not completely (homogeneously) miscible under application conditions, and
at least one polymer block P(E) is miscible with P(A).

Quality and Detection of Microphase Separation

Typical methods of determining the existence of microphase separation include for example:
transmission electron microscopy (TEM) in the case of materials which interact differently with staining agents;
atomic force microscopy (AFM) by way of the surface topology, a contrast in hardness or in adhesion;
scattering methods (neutron scattering, small-angle X-ray scattering) in the case of materials with phases which show a difference in the material/radiation effect cross-section;
calorimetric methods, such as differential thermocalorimetry (DSC) or differential thermal analysis (DTA) and also rheological measurements for materials with phases of different softening points;

NMR spin diffusion for materials with phases differing in dynamics.

The microphase separation observed in PSAs of the invention only in the limiting case yields the ideal structures such as are frequently described, for example, in the classic phase diagrams of block copolymers (see e.g. H. G. Elias in "Makromoleküle"; Wiley-VCH, 6th Edition 2001, Volume 2, section 8.5.2 or I. W. Hamley, The Physics of Block Copolymers, 1998, Oxford University Press, Oxford). This is also not at all desirable in all cases, since controlling the quality of microphase separation makes it possible advantageously to influence the adhesives properties of the PSAs.

Monomers

The monomers A for the polymer blocks P(A) and/or the copolymer blocks P(A/C) and monomers B for the polymer blocks P(B) and/or the copolymer blocks P(B/D) or monomers E for the polymer blocks P(E) and/or the copolymer blocks P(E/F) of the PSAs used in accordance with the invention are preferably chosen such that the blocks interlinked in the block copolymer are not completely (homogeneously) miscible with one another and, consequently, form a two-phase structure. This structure includes domains composed of miscible block segments (including whole blocks in the ideal case) of different (and possibly also identical) chains. Prerequisites for miscibility are a chemically similar construction of these block segments or blocks and block lengths adapted to one another. The domains adopt a particular shape and superstructure depending on the volume fraction of a phase within the system as a whole. Depending on the choice of monomers used it is possible for the domains to differ in their softening/ glass transition temperatures, their hardness and/or their polarity.

The monomers employed in the polymer blocks or polymers P(A), P(B) and P(E) and in the copolymer blocks or polymers P(A/C), P(B/D) and P(E/F) are taken from the same monomer pool described below. Within a blend it is possible for the monomers to be chosen identically or differently, provided that in this case chemically different individual components $K_c$ and $L_D$ and, within a block copolymer, chemically different polymer blocks are produced.

For the PSAs of the invention described here it is advantageous to use acrylic monomers, methacrylic monomers and/ or vinyl monomers, more preferably those monomers which lower the softening/glass transition temperature of the copolymer block P(A/C)—also in combination with monomer C—or of the copolymer block P(B/D)—also in combination with monomer D—or of the copolymer block P(E/ F)—also in combination with monomer F—to below 20° C.

When selecting the monomers for the PSA of the invention great advantage attaches to using one or more compounds which can be described by the following general formula.

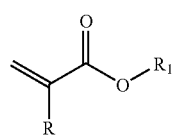

(IV)

In this formula R=H or $CH_3$ and the radical $R_1$ is selected from the group consisting of branched and unbranched, saturated alkyl groups having 1 to 20 carbon atoms.

Acrylic or methacrylic monomers which are used with preference for the inventive PSA as monomers A, B, or E include acrylic and methacrylic esters with alkyl groups consisting of 1 to 18 carbon atoms, preferably 4 to 9 carbon atoms. Specific examples, without wishing to be restricted by this enumeration, are methyl acrylate, ethyl acrylate, n-propyl acrylate, n-butyl acrylate, n-pentyl acrylate, n-hexyl acrylate, n-heptyl acrylate, n-octyl acrylate, n-nonyl acrylate, lauryl acrylate, stearyl acrylate and their branched isomers, such as 2-ethylhexyl acrylate, isobutyl acrylate and isooctyl acrylate, for example.

Further monomers to be used for the polymer blocks P(A), P(B) and P(E) and copolymer blocks P(A/C), P(B/D) and P(E/F) are monofunctional acrylates and methacrylates of bridged cycloalkyl alcohols composed of at least 6 carbon atoms. The cycloalkyl alcohols may also be substituted. Specific examples are cyclohexyl methacrylate, isobornyl acrylate, isobornyl methacrylate and 3,5-dimethyladamantyl acrylate.

Additionally use is made optionally, for the polymer blocks P(A), P(B) and/or P(E) and copolymer blocks P(A/C), P(B/ D) and P(E/F), of vinyl monomers from the group consisting of the vinyl esters, vinyl ethers, vinyl halides, vinylidene halides, vinyl compounds containing aromatic rings and heterocycles in α position. Here again mention may be made non-exclusively of some examples: vinyl acetate, vinylformamide, ethyl vinyl ether, vinyl chloride, vinylidene chloride and acrylonitrile.

When synthesizing the block copolymers of the invention it is necessary to ensure when selecting the monomer combinations that the polymer blocks prepared from the monomers used are not completely miscible with one another.

The monomers B of the acrylate block copolymers of the invention embrace the group of the monomers A. In one preferred version the monomer B for the polymer block B is different from the polymer A for the polymer block P(A). For the case of interpretation whereby two or more monomers are used for the polymer blocks P(A) or P(B), the monomers B are different from the monomers A or differ in their composition from the monomers A. In another preferred version the monomers B that are used differ from the monomers A in their number.

In a further preferred procedure the monomers used as comonomers C, D and F for the copolymer blocks P(A/C), P(B/D) and P(E/F) are vinyl compounds, acrylates and/or methacrylates and/or acrylamides and/or methacrylamides which preferably carry functional and/or polar groups, in particular carboxyl radicals, sulphonic and phosphonic acid groups, hydroxy radicals, lactam and lactone, N-substituted amide, N-substituted amine, carbamate, epoxy, thiol, alkoxy or cyano radicals, ethers, halides or the like.

Very advantageously for the PSA of the invention the monomers used as monomers C, D and F for the copolymer blocks P(A/C), P(B/D) and P(E/F) comprise one or more monomers having at least one functional and/or polar group which can be described by the following general formula (V).

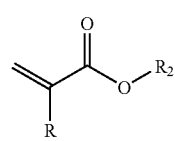

(V)

In this formula R=H or $CH_3$ and the radical $R_2$=H or an organic radical containing at least one functional and/or polar group and containing between 1 and 30 carbon atoms.

Particularly preferred examples of corresponding monomers containing vinyl groups suitably include, for example, acrylic acid, hydroxyethyl acrylate, hydroxyethyl methacrylate, hydroxypropyl acrylate, hydroxypropyl methacrylate, N-methylolacrylamide, methacrylic acid, allyl alcohol, maleic anhydride, itaconic anhydride, itaconic acid, phenoxyethyl acrylate, phenoxyethyl methacrylate, 2-butoxyethyl acrylate, 2-butoxyethyl methacrylate, cyanoethyl acrylate, cyanoethyl methacrylate, 6-hydroxyhexyl methacrylate, tetrahydrofurfuryl acrylate, acrylamide and glycidyl methacrylate.

Moderate basic monomers C, D and F for the copolymer blocks P(A/C), P(B/D) and P(E/F) are, for example, N,N-dialkyl-substituted amides, such as N,N-dimethylacrylamide, N,N-dimethylmethacrylamide, N-vinylpyrrolidone, N-vinyllactam, dimethylaminoethyl acrylate, dimethylaminoethyl methacrylate, diethylaminoethyl acrylate, diethylaminoethyl methacrylate, N-methylolacrylamide, N-methylolmethacrylamide, N-(butoxymethyl)methacrylamide, N-(ethoxymethyl)acrylamide, and N-isopropylacrylamide, this enumeration being intended to be regarded as by way of example.

As monomers C, D and F for the copolymer blocks P(A/C), P(B/D) and P(E/F) it is additionally possible to use vinylphosphonic acid, vinylsulphonic acid and the sodium salt of vinylsulphonic acid.

As monomers C, D and F for the copolymer blocks P(A/C), P(B/D) and P(E/F) it is also possible, furthermore, to use zwitterionic monomers, such as the group of the betaines, for example. Examples of suitable betaines include ammonium carboxylates, ammonium phosphates and ammonium sulphonates. Specific examples are N-(3-sulphopropyl)-N-acryloyloxyethyl-N,N-dimethylammonium betaine, 1-(3-sulphopropyl)-2-vinylpyridinium betaine and N-(3-sulphopropyl)-N-allyl-N,N-dimethylammonium betaine. Particularly preferred examples are N-(3-sulphopropyl)-N-methacryloyloxyethyl-N,N-dimethyl-ammonium betaine and N-(3-sulphopropyl)-N-acryloyloxyethyl-N,N-dimethylammonium betaine. N-(3-sulphopropyl)-N-methacryloxyethyl-N,N-dimethylammonium betaine is available commercially from Raschig AG, Germany. This enumeration likewise possesses no claim to completeness.

Likewise suitable as monomers C, D and F for the copolymer blocks P(A/C), P(B/D) and P(E/F) are (meth)acrylic monomers or vinyl monomers which increase the softening/glass transition temperature of the copolymer block P(A/C)—also in combination with monomer A—and/or of the copolymer block P(B/D)—also in combination with monomer B—and/or of the copolymer block P(E/F)—also in combination with monomer E.

Examples of corresponding monomers C, D and F are hence also methyl methacrylate, cyclohexyl methacrylate, t-butyl acrylate, isobornyl methacrylate, benzyl acrylate, benzoin acrylate, acrylated benzophenone, benzyl methacrylate, benzoin methacrylate, methacrylated benzophenone, phenyl acrylate, phenyl methacrylate, t-butylphenyl acrylate, t-butylphenyl methacrylate, 4-biphenylyl acrylate, 2-naphthyl acrylate and 2-naphthyl methacrylate, and styrene, this enumeration not being conclusive.

Vinylaromatic monomers C, D and F for the copolymer blocks P(A/C), P(B/D) and P(E/F), which may also be alkylated, functionalized or contain heteroatoms and which preferably possess aromatic nuclei of $C_4$ to $C_{18}$, also include α-methylstyrene, 4-vinylbenzoic acid, the sodium salt of 4-vinylbenzenesulphonic acid, 4-vinylbenzyl alcohol, 2-vinylnaphthalene, 4-vinylphenylboronic acid, 4-vinylpyridine, phenyl vinylsulphonate, 3,4-dimethoxystyrene, vinyl benzotrifluoride, p-methoxystyrene, 4-vinylanisole, 9-vinylanthracene, 1-vinylimidazole, 4-ethoxystyrene, and N-vinylphthalimide, this enumeration making no claim to completeness.

Polymerizations

The polymerization can be carried out by any method known per se or in modification of a method known per se, in particular by means of conventional free-radical addition polymerization and/or by means of controlled free-radical addition polymerization; the latter is characterized by the presence of suitable control reagents.

To prepare the block copolymers it is possible in principle to use all polymerizations which proceed in accordance with a controlled or living mechanism, including combinations of different controlled polymerization methods. Without possessing any claim to completeness, mention may be made here, by way of example, besides anionic polymerization, of ATRP, nitroxide/TEMPO-controlled polymerization or, more preferably, the RAFT process; in other words, particularly those methods which allow control over the block lengths, polymer architecture or else, but not necessarily, the tacticity of the polymer chain.

Radical polymerizations can be conducted in the presence of an organic solvent or in the presence of water or in mixtures of organic solvents and/or organic solvent with water, or without solvent. When carrying out the polymerization in organic solvents it is preferred to use as little solvent as possible. Depending on conversion and temperature, the polymerization time for radical processes is typically between 4 and 72 h.

In the case of solution polymerization the solvents used are preferably esters of saturated carboxylic acids (such as ethyl acetate), aliphatic hydrocarbons (such as n-hexane, n-heptane or cyclohexane), ketones (such as acetone or methyl ethyl ketone), special boiling point spirit, aromatic solvents such as toluene or xylene, or mixtures of aforementioned solvents. For polymerization in aqueous media or in mixtures of organic and aqueous solvents it is preferred to add emulsifiers and/or stabilizers for the polymerization.

Where a method of radical polymerization is employed it is advantageous to make use, as polymerization initiators, of customary radical-forming compounds, such as peroxides, azo compounds and peroxosulphates, for example. Initiator mixtures also possess outstanding suitability.

In an advantageous procedure radical stabilization is effected using nitroxides of type (VIa) or (VIb):

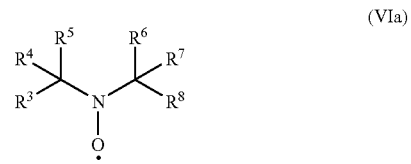

(VIa)

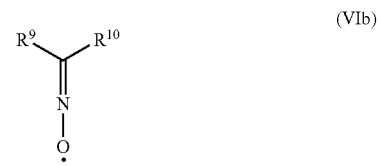

(VIb)

where $R^3, R^4, R^5, R^6, R^7, R^8, R^9$ and $R^{10}$ independently of one another denote the following compounds or atoms:

i) halogens, such as chlorine, bromine or iodine;

ii) linear, branched, cyclic and heterocyclic hydrocarbons having 1 to 20 carbon atoms, which can be saturated, unsaturated or aromatic;

iii) esters —COOR$^{11}$, alkoxides —OR$^{12}$ and/or phosphonates —PO(OR$^{13}$)$_2$, where R$^{11}$, R$^{12}$ or R$^{13}$ stand for radicals from group ii).

Compounds of structure (VIa) or (VIb) may also be attached to polymer chains of any kind (primarily in the sense that at least one of the abovementioned radicals constitutes such a polymer chain) and can therefore be used as macroradicals or macroregulators to construct the block copolymers.

More preferred as controlled regulators for the polymerization are compounds of the type:

2,2,5,5-tetramethyl-1-pyrrolidinyloxyl (PROXYL), 3-carbamoyl-PROXYL, 2,2-dimethyl-4,5-cyclohexyl-PROXYL, 3-oxo-PROXYL, 3-hydroxylimine-PROXYL, 3-aminomethyl-PROXYL, 3-methoxy-PROXYL, 3-t-butyl-PROXYL, 3,4-di-t-butyl-PROXYL;

2,2,6,6-tetramethyl-1-piperidinyloxyl (TEMPO), 4-benzoyloxy-TEMPO, 4-methoxy-TEMPO, 4-chloro-TEMPO, 4-hydroxy-TEMPO, 4-oxo-TEMPO, 4-amino-TEMPO, 2,2,6,6-tetraethyl-1-piperidinyloxyl, 2,2,6-trimethyl-6-ethyl-1-piperidinyloxyl;

N-tert-butyl 1-phenyl-2-methylpropyl nitroxide;

N-tert-butyl 1-(2-naphthyl)-2-methylpropyl nitroxide;

N-tert-butyl 1-diethylphosphono-2,2-dimethylpropyl nitroxide;

N-tert-butyl 1-dibenzylphosphono-2,2-dimethylpropyl nitroxide;

N-(1-phenyl-2-methylpropyl) 1-diethylphosphono-1-methylethyl nitroxide;

di-t-butyl nitroxide;

diphenyl nitroxide;

t-butyl t-amyl nitroxide.

U.S. Pat. No. 4,581,429 A discloses a controlled-growth radical polymerization method initiated using a compound of formula R'R"N—O—Y in which Y is a free-radical species which is able to polymerize unsaturated monomers. The reactions, however, generally have low conversions. A particular problem is the polymerization of acrylates, which proceeds only to very low yields and molar masses. WO 98/13392 A1 describes open-chain alkoxyamine compounds which have a symmetrical substitution pattern. EP 735 052 A1 discloses a method of preparing thermoplastic elastomers having narrow molar mass distributions. WO 96/24620 A1 describes a polymerization method using very specific radical compounds, such as phosphorus-containing nitroxides based on imidazolidine, for example. WO 98/44008 A1 discloses specific nitroxyls based on morpholines, piperazinones and piperazinediones. DE 199 49 352 A1 describes heterocyclic alkoxyamines as regulators in controlled-growth radical polymerizations. Corresponding further developments of the alkoxyamines and of the corresponding free nitroxides improve the efficiency for preparing polyacrylates (Hawker, contribution to the National Meeting of the American Chemical Society, Spring 1997; Husemann, contribution to the IUPAC World-Polymer Meeting 1998, Gold Coast).

As a further controlled polymerization technique it is possible advantageously to use atom transfer radical polymerization (ATRP) to synthesize the block copolymers, with preferably monofunctional or difunctional secondary or tertiary halides being used as initiator and, to abstract the halide(s), complexes of Cu, Ni, Fe, Pd, Pt, Ru, Os, Rh, Co, Ir, Ag or Au (EP 0 824 111 A1; EP 826 698 A1; EP 824 110 A1; EP 841 346 A1; EP 850 957 A1). The different possibilities of ATRP are also described in the publications U.S. Pat. No. 5,945,491 A, U.S. Pat. No. 5,854,364 A and U.S. Pat. No. 5,789,487 A.

In a further controlled polymerization method 1,1-diphenylethylene is used as a control reagent. The preparation of block copolymers by this route has likewise been described (Macromol. Chem. Phys., 2001, 22, 700).

It is additionally possible with advantage to prepare the block copolymer utilized in accordance with the invention by means of an anionic polymerization. In this case the reaction medium used preferably comprises inert solvents, such as aliphatic and cycloaliphatic hydrocarbons, for example, or else aromatic hydrocarbons.

The living polymer is generally represented by the structure P$_L$(A)-Me, in which Me is a metal from group I, such as lithium, sodium or potassium, and P$_L$(A) is a growing polymer block of the monomers A. The molar mass of the polymer block under preparation is determined by the ratio of initiator concentration to monomer concentration. In order to construct the block structure, first of all the monomers A are added for the construction of a polymer block P(A), then, by adding the monomers B, a polymer block P(B) is attached, and subsequently, by again adding monomers A, a further polymer block P(A) is polymerized on, so as to form a triblock copolymer P(A)-P(B)-P(A). Alternatively P(A)-P(B)-M can be coupled by means of a suitable difunctional compound. By this route star-shaped multiblock copolymers of formula (II) as well are obtainable.

Examples of suitable polymerization initiators include n-propyllithium, n-butyllithium, sec-butyllithium, 2-naphthyllithium, cyclohexyllithium or octyllithium, this enumeration making no claim to completeness. Also known, and suitable for use here, are initiators based on rare earth element complexes for the polymerization of acrylates (Macromolecules, 1995, 28, 7886).

It is also possible, moreover, to use difunctional initiators, such as 1,1,4,4-tetraphenyl-1,4-dilithiobutane or 1,1,4,4-tetraphenyl-1,4-dilithioisobutane, for example. Coinitiators may likewise be used. Suitable coinitiators include lithium halides, alkali metal alkoxides or alkylaluminium compounds. In one very preferred version the ligands and coinitiators are chosen so that acrylate monomers, such as n-butyl acrylate and 2-ethylhexyl acrylate, can be polymerized directly and do not have to be generated in the polymer by transesterification with the corresponding alcohol.

After the anionic polymerization it is advisable to carry out a polymer-analogous reaction in order to liberate polar groups. One possibility for preparing acrylate block copolymers functionalized with carboxylic acid groups involves the anionic polymerization of tert-butyl acrylate followed if desired by hydrolysis of the tert-butyl group with trifluoroacetic acid, thereby liberating the carboxylic acid group.

A very preferred preparation process conducted is a variant of the RAFT polymerization (reversible addition-fragmentation chain transfer polymerization). The polymerization process is described in detail, for example, in the publications WO 98/01478 A1 and WO 99/31144 A1. Suitable with particular advantage for the preparation of triblock copolymers are trithiocarbonates of the general structure R'''—S—C(=S)—S—R''' (Macromolecules 2000, 33, 243-245), by means of which, in a first step, monomers for the end blocks P(A) are polymerized. Then, in a second step, the central block P(B) is synthesized. Following the polymerization of the end blocks P(A) the reaction can be terminated and reinitiated. It is also possible to carry out polymerization sequentially without interrupting the reaction. In one very advantageous variant, for example, the trithiocarbonates (VII) and (VIII) or the thio compounds (IX) and (X) are used for the polymerization, it being possible for φ to be a phenyl ring, which can be unfunctionalized or functionalized by alkyl or aryl substituents attached directly or via ester or ether bridges, or to be a cyano group, or to be a saturated or unsaturated aliphatic radical. The phenyl ring φ may optionally carry one or more polymer blocks, corresponding to the definition of P(A), P(B), P(A/C) and P(B/D). Functionalizations may, for example, be halogens, hydroxyl groups, epoxide groups, groups containing nitrogen or sulphur, with this list making no claim to completeness.

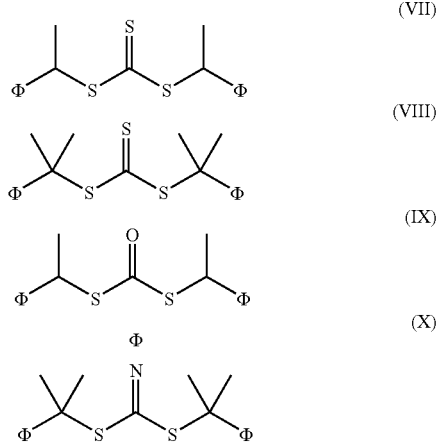

It is additionally possible to employ thioesters of the general structure $R^{IV}$—C(=S)—S—$R^V$, particularly in order to prepare asymmetric systems. $R^{IV}$ and $R^V$ can be selected independently of one another and $R^{IV}$ can be a radical from one of the following groups i) to iv) and $R^V$ a radical from one of the following groups i) to iii):

i) $C_1$ to $C_{18}$ alkyl, $C_2$ to $C_{18}$ alkenyl, $C_2$ to $C_{18}$ alkynyl, each linear or branched; aryl-, phenyl-, benzyl-, aliphatic and aromatic heterocycles, ii) —$NH_2$, —NH—$R^{VI}$, —$NR^{VI}R^{VII}$, —NH—C(=O)—$R^{VI}$, —$NR^{VI}$—C(=O)—$R^{VII}$, —NH—C(=S)—$R^{VI}$, —$NR^{VI}$—C(=S)—$R^{VII}$,

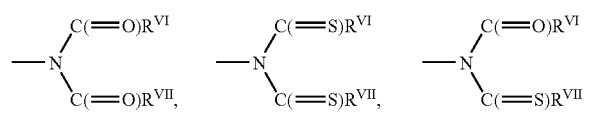

with $R^{VI}$ and $R^{VII}$ being radicals selected independently of one another from group i), iii) —S—$R^{VIII}$, —S—C(=S)—$R^{VIII}$, with $R^{VIII}$ being able to be a radical from one of groups i) and ii), iv) —O—$R^{VIII}$, —O—C(=O)—$R^{VIII}$, with $R^{VIII}$ being able to be a radical from one of groups i) and ii).

In connection with the abovementioned polymerizations which proceed by controlled radical mechanisms it is preferred to use initiator systems which further comprise additional radical initiators for the polymerization, especially thermally decomposing radical-forming azo or peroxo initiators. In principle, however, all customary initiators known for acrylates are suitable for this purpose. The production of C-centred radicals is described in Houben-Weyl, Methoden der Organischen Chemie, Vol. E19a, p. 60ff. These methods are preferentially employed. Examples of radical sources are peroxides, hydroperoxides and azo compounds. A few non-exclusive examples of typical radical initiators that may be mentioned here include the following: potassium peroxodisulphate, dibenzoyl peroxide, cumene hydroperoxide, cyclohexanone peroxide, cyclohexyl-sulphonyl acetyl peroxide, di-tert-butyl peroxide, azodiisobutyronitrile, diisopropyl percarbonate, tert-butyl peroctoate, and benzpinacol. In one very preferred variant the radical initiator used is 1,1'-azobis(cyclohexylnitrile) (Vazo 88®, DuPont®) or 2,2-azobis(2-methylbutanenitrile) (Vazo 67®, DuPont®). It is also possible, furthermore, to use radical sources which release radicals only under UV irradiation.

In the case of the conventional RAFT process polymerization is generally carried out only to low conversions (WO 98/01478 A1), in order to obtain very narrow molecular weight distributions. Because of the low conversions, however, these polymers cannot be used as pressure-sensitive adhesives and in particular not as hotmelt adhesives, since the high residual monomer fraction adversely affects the adhesives properties, the residual monomers contaminate the solvent recyclate in the concentration process, and the corresponding self-adhesive tapes would exhibit very high outgassing. In accordance with the invention, therefore, the solvent is preferably stripped off in a concentrative extruder under reduced pressure, for which purpose it is possible to use, for example, single-screw or twin-screw extruders, which preferably distil off the solvent in different or the same vacuum stages and which preferably possess a feed preheater.

For advantageous further development, tackifing resins can be admixed to the block copolymer PSAs. In principle it is possible to use all resins soluble in the corresponding polyacrylate blocks P(A) and P(AC) or P(B) and P(B/D) or P(E) and P(E/F), respectively. Suitable tackifying resins include rosin and rosin derivatives (rosin esters, including rosin derivatives stabilized by means, for example, of disproportionation or hydrogenation), polyterpene resins, terpenephenolic resins, alkylphenol resins, aliphatic, aromatic and aliphatic-aromatic hydrocarbon resins, to name but a few. The weight fraction of the resins as a proportion of the PSA is, in this case, up to 60% by weight, more preferably up to 50% by weight. For one specific way of carrying out the invention it is also possible to use resins which specifically are compatible in only one, or one part, of the polymer blocks P(A) and P(A/C) and/or P(B) and P(B/D) and/or P(E) and P(E/F), respectively.

It is additionally possible, optionally, to use plasticizers, fillers (e.g. fibers (e.g. cellulose fibres or polyvinyl alcohol fibres), carbon black, zinc oxide, titanium dioxide, chalk, solid or hollow glass beads, microspheres of other materials, silica, silicates), nucleators, expandants, compounding agents and/or ageing inhibitors, in the form for example of primary and secondary antioxidants or in the form of light stabilizers.

In one particularly preferred version the inventive PSAs are crosslinked. The PSAs are preferably crosslinked chemically. For this purpose it is possible optionally to add compatible crosslinker substances to the acrylate block copolymer PSAs. Examples of suitable crosslinkers include metal chelates, polyfunctional isocyanates, polyfunctional amines, polyfunctional epoxides or polyfunctional alcohols. Polyfunctional acrylates too can be used with advantage as crosslinkers for actinic irradiation.

For the optional crosslinking with UV light, UV-absorbing photoinitiators are added to the acrylate block copolymers. Useful photoinitiators which can be used to great effect are benzoin ethers, such as benzoin methyl ether and benzoin isopropyl ether, substituted acetophenones, such as 2,2-diethoxyacetophenone (available as Irgacure 651® from Ciba Geigy®), 2,2-dimethoxy-2-phenyl-1-phenylethanone and dimethoxyhydroxyacetophenone, substituted α-ketols, such as 2-methoxy-2-hydroxypropiophenone, aromatic sulphonyl chlorides, such as 2-naphthylsulphonyl chloride, and photoactive oximes, such as 1-phenyl-1,2-propanedione 2-(O-ethoxycarbonyl) oxime, for example.

The abovementioned photoinitiators and others which can be used, including those of the Norrish I or Norrish II type, can contain the following radicals: benzophenone, acetophenone, benzil, benzoin, hydroxyalkylphenone, phenyl cyclohexyl ketone, anthraquinone, trimethylbenzoylphosphine oxide, methylthiophenyl morpholinyl ketone, amino ketone, azo benzoin, thioxanthone, hexaarylbisimidazole, triazine, or fluorenone, it being possible for each of these radicals to be further substituted by one or more halogen atoms and/or one or more alkyloxy groups and/or one or more amino groups or hydroxyl groups. A representative overview is given by Fouassier: "Photoinititation, Photopolymerization and Photocuring: Fundamentals and Applications", Hanser-Verlag, Munich 1995. For further details it is possible to consult Carroy et al. in "Chemistry and Technology of UV and EB Formulation for Coatings, Inks and Paints", Oldring (Ed.), 1994, SITA, London.

Moreover, it is also possible to crosslink the inventive acrylate block copolymers using electron beams. Typical irradiation devices which may be employed are linear cathode systems, scanner systems and segmented cathode systems, in the case of electron beam accelerators. A detailed description of the state of the art and the most important process parameters can be found in Skelhorne, Electron Beam Processing, in Chemistry and Technology of UV and EB formulation for Coatings, Inks and Paints, Vol. 1, 1991, SITA, London. The typical acceleration voltages are in the range between 50 kV and 500 kV, preferably between 80 kV and 300 kV. The scatter doses employed range between 5 to 150 kGy, in particular between 20 and 100 kGy.

Test Methods

180° Bond Strength Test (Test A)

A strip 20 mm wide of a PSA coated onto siliconized release paper was transferred by lamination to a PET film, 25 μm thick and provided with a Saran primer, and then this PSA tape specimen was applied to a steel plate. The steel plates had been washed beforehand twice with acetone and once with isopropanol. The PSA strip was pressed down twice onto the substrate using a 2 kg weight. The adhesive tape was then immediately removed from the substrate at 30 mm/min and at an angle of 180°. The results of the measurements are reported in N/cm and represent the mean of three individual measurements. All measurements were conducted at room temperature under standardized climatic conditions.

Gel Permeation Chromatography (GPC) (Test B)

The average molecular weights $M_n$ (number average) and $M_w$ (weight average) and the polydispersity D were determined by gel permeation chromatography. The eluent used was THF containing 0.1% by volume trifluoroacetic acid. Measurement took place at 25° C. The precolumn used was PSS-SDV, 5μ, $10^3$ Å, ID 8.0 mm×50 mm. Separation was carried out using the columns PSS-SDV, 5μ, $10^3$ and also $10^5$ and $10^6$ Å each of ID 8.0 mm×300 mm. The sample concentration was 4 g/l, the flow rate 1.0 ml per minute. Measurement was made against PMMA standards.

Shear Stability Times (Test C)

Testing took place according to PSTC-107. A 50 μm layer of pressure-sensitive adhesive was applied to a 25 μm PET film. A strip of this sample 1.3 cm thick was adhered to a polished steel plate over a length of 2 cm, by rolling over it back and forth three times using a 2 kg roller. The plates were equilibrated for 30 minutes under test conditions (temperature and humidity) but without loading. Then the test weight was hung on, exerting a shearing stress parallel to the bond surface, and the time taken for the bond to fail was measured. If a holding time of 10 000 minutes was reached, the test was discontinued before failure of the adhesive bond.

Differential Thermocalorimetry (DSC) (Test D)

The measurements were made using a dynamic power-compensation differential calorimeter from Mettler Toledo. The measurement took place within a temperature range from −150 to 180° C. The heating rate was 10° C./min. Two heating curves were measured in each case, the second heating curve being used to determine the onset glass transition temperature.

Production of Test Specimens

Preparation of a RAFT Regulator:

The bis-2,2'-phenylethyl trithiocarbonate regulator (formula VIII) was prepared starting from 2-phenylethyl bromide using carbon disulphide and sodium hydroxide in accordance with a set of instructions in Synth. Comm., 1988, 18 (13), 1531.

The yield was 72% and the following $^1$H-NMR signals were measured in $CDCl_3$: δ: 7.20-7.40 ppm (m, 10H); 3.81 ppm (m, 1H); 3.71 ppm (m, 1H); 1.59 ppm (d, 3H); 1.53 ppm (d, 3H).

Preparation of the Components $K_c$

EXAMPLE K1

A 2 l reactor conventional for radical polymerization is charged under a nitrogen atmosphere with 30 g of acrylic acid, 50 g of 2-ethylhexyl acrylate, 1.2 g of bis-2,2'-phenylethyl trithiocarbonate regulator and 80 g of acetone. This initial charge was heated to an internal temperature of 60° C. and initiated with 0.2 g of Vazo 67® (DuPont) in solution in 5 g of acetone. After a reaction time of 1.5 hours initiation was repeated with 0.2 g of Vazo 67® (DuPont) in solution in 5 g of acetone. After a reaction time of 5 hours and 7 hours dilution was carried out, with 50 g of acetone each time.

After a reaction time of 24 hours a sample is taken. Gel permeation chromatography (test B) against PMMA standards gave $M_n$=32 200 g/mol and $M_w$=36 700 g/mol. The quasistatic glass transition temperature measured by DSC (test D) for this polymer block was −4° C.

Polymerization was continued in the same reactor after a reaction time of 24 h. Added to the polymer were 320 g of 2-ethylhexyl acrylate, 80 g of acetone and 20 g of isopropanol. After a reaction time of 24.75 hours initiation was repeated with 0.2 g of Vazo 67® (DuPont) in solution in 5 g of acetone. After 28.5 hours and 32 hours dilution was carried out with acetone, 50 g in each case. After 48 hours initiation was repeated with 0.2 g of Vazo 67® (DuPont) in solution in 5 g of acetone. After 55.5 hours 20 g of acetone were added and after 72 hours the reaction was terminated by cooling to room temperature.

Gel permeation chromatography (test B) against PMMA standards gave $M_n$=48 600 g/mol and $M_w$=83 500 g/mol. The quasistatic glass transition temperature for the poly(2-EHA) block measured by DSC (test D) for this polymer block was −65° C.

EXAMPLE K2

A 2 l reactor conventional for radical polymerization is charged under a nitrogen atmosphere with 16 g of acrylic acid, 64 g of 2-ethylhexyl acrylate, 1.2 g of bis-2,2'-phenylethyl trithiocarbonate regulator and 120 g of acetone. This initial charge was heated to an internal temperature of 60° C. and initiated with 0.1 g of Vazo 67® (DuPont) in solution in 5 g of acetone. After 1 hour and 15 minutes a further 0.1 g of Vazo 67® (DuPont) in solution in 5 g of acetone was added. After 2 hours and 55 minutes 0.15 g of Vazo 67® (DuPont) in solution in 5 g of acetone was added and after a reaction time of 4 hours and 25 minutes a further 0.1 g of Vazo 67® (DuPont) in solution in 5 g of acetone.

After 24 h a sample was taken. Carrying out gel permeation chromatography (test B) against PMMA standards gave $M_n$=20 200 g/mol and $M_w$=25 600 g/mol. The quasistatic glass transition temperature measured by DSC (test D) for this polymer block was −33° C.

The polymerization was continued in the same reactor after a reaction time of 24 h. Added to the polymer were 320 g of 2-ethylhexyl acrylate and 0.2 g of Vazo 67® (DuPont) in solution in 5 g of acetone. After a total reaction time of 30 hours dilution was carried out with 150 g of acetone. After a reaction time of 48 h, initiation was repeated with and 0.2 g of Vazo 67® (DuPont) in solution in 5 g of acetone. The polymerization was terminated after 7 h by cooling to room temperature.

Carrying out gel permeation chromatography (test B) against PMMA standards gave $M_n$=66 400 g/mol and $M_w$=109 000 g/mol. The quasistatic glass transition temperature for the poly(2-EHA) block measured by DSC (test D) for this polymer block was −65° C.

Preparation of the Components $L_D$

EXAMPLE L1

A 2 l reactor conventional for radical polymerization was charged under a nitrogen atmosphere with 30 g of acrylic acid, 50 g of 2-ethylhexyl acrylate, 1.2 g of bis-2,2'-phenylethyl trithiocarbonate regulator and 80 g of acetone. This initial charge was heated to an internal temperature of 60° C. and initiated with 0.2 g of Vazo 67® (DuPont) in solution in 5 g of acetone. After a reaction time of 1.5 hours initiation was repeated with 0.2 g of Vaso 67® (DuPont) in solution in 5 g of acetone. After 5 and 7 hours' reaction time dilution was carried out with acetone, 50 g in each case.

After a reaction time of 24 hours the polymerization was terminated by cooling to room temperature. Carrying out gel permeation chromatography (test B) against PMMA standards gave $M_n$=32 200 g/mol and $M_w$=36 700 g/mol. The quasistatic glass transition temperature measured by DSC (test D) for this polymer block was −4° C.

EXAMPLE L2

A 2 l reactor conventional for radical polymerization was charged under a nitrogen atmosphere with 80 g of 2-ethylhexyl acrylate, 1.2 g of bis-2,2'-phenylethyl trithiocarbonate regulator and 80 g of acetone. This initial charge was heated to an internal temperature of 60° C. and initiated with 0.2 g of Vazo 67® (DuPont) in solution in 5 g of acetone. After a reaction time of 1.5 hours initiation was repeated with 0.2 g of Vaso 67® (DuPont) in solution in 5 g of acetone. After 5 and 7 hours' reaction time dilution was carried out with special boiling point spirit 60/95, 50 g in each case.

After a reaction time of 24 hours the polymerization was terminated by cooling to room temperature. Carrying out gel permeation chromatography (test B) against PMMA standards gave $M_n$=33 400 g/mol and $M_w$=38 700 g/mol. The quasistatic glass transition temperature measured by DSC (test D) for this polymer block was −65° C.

EXAMPLE L3

A 2 l reactor conventional for radical polymerization was charged under a nitrogen atmosphere with 80 g of 2-ethylhexyl acrylate, 1.2 g of bis-2,2'-phenylethyl trithiocarbonate regulator and 120 g of acetone. This initial charge was heated to an internal temperature of 60° C. and initiated with 0.1 g of Vazo 67® (DuPont) in solution in 5 g of acetone. After one hour and 15 minutes a further 0.1 g of Vaso 67® (DuPont) in solution in 5 g of acetone was added. After 2 hours and 55 minutes 0.15 g of Vaso 67® (DuPont) in solution in 5 g of acetone was added, and after a reaction time of 4 hours and 25 minutes a further 0.1 g of Vaso 67® (DuPont) in solution in 5 g of acetone.

After 24 h a sample was taken. Carrying out gel permeation chromatography (test B) against PMMA standards gave $M_n$=25 600 g/mol and $M_w$=30 200 g/mol. The quasistatic glass transition temperature measured by DSC (test D) for this polymer block was −65° C.

The polymerization was continued in the same reactor after a reaction time of 24 h. Added to the polymer were 64 g of acrylic acid, 256 g of 2-ethylhexyl acrylate and 0.2 g of Vaso 67® (DuPont) in solution in 5 g of acetone. After a total reaction time of 30 hours dilution was carried out with 150 g of acetone. After a reaction time of 48 h initiation was repeated with 0.2 g of Vaso 67® (DuPont) in solution in 5 g of acetone. The polymerization was terminated after 72 h by cooling to room temperature.

Carrying out gel permeation chromatography (Test B) against PMMA standards gave $M_n$=73 200 g/mol and $M_w$=122 000 g/mol. The quasistatic glass transition temperature for the poly(AA/2-EHA) block measured by DSC (test D) for this polymer block was −31° C.

EXAMPLE L4

A 2 l reactor conventional for radical polymerization was charged under a nitrogen atmosphere with 80 g of 2-ethylhexyl acrylate, 1.2 g of bis-2,2'-phenylethyl trithiocarbonate regulator and 120 g of acetone. This initial charge was heated to an internal temperature of 60° C. and initiated with 0.1 g of Vazo 67® (DuPont) in solution in 5 g of acetone. After one hour and 15 minutes a further 0.1 g of Vaso 67® (DuPont) in solution in 5 g of acetone was added. After 2 hours and 55 minutes 0.15 g of Vaso 67® (DuPont) in solution in 5 g of acetone was added, and after a reaction time of 4 hours and 25 minutes a further 0.1 g of Vaso 67® (DuPont) in solution in 5 g of acetone.

After 24 h a sample was taken. Carrying out gel permeation chromatography (test B) against PMMA standards gave $M_n$=25 600 g/mol and $M_w$=30 200 g/mol. The quasistatic glass transition temperature measured by DSC (test D) for this polymer block was −65° C.

The polymerization was continued in the same reactor after a reaction time of 24 h. Added to the polymer were 200 g of 2-ethylhexyl acrylate, 120 g of acrylic acid, 80 g of acetone and 20 g of isopropanol. After a reaction time of 24 hours initiation was repeated with 0.2 g Vaso 67® (DuPont) in solution in 5 g of acetone. After 28 and 32 hours dilution was carried out with acetone, 50 g in each case. After 48 hours initiation was repeated with 0.2 g of Vaso 67® (DuPont) in solution in 5 g of acetone. After 60 hours 20 g of acetone were added and after 72 hours the reaction was terminated by cooling to room temperature.

Carrying out gel permeation chromatography (test B) against PMMA standards gave $M_n=56\,300$ g/mol and $M_n=92\,100$ g/mol. The quasistatic glass transition temperature for the poly(AA/2-EHA) block measured by DSC (test D) for this polymer block was +2° C.

Polymer Blending:

The polymer blending with components $K_c$ and $L_D$ took place in 25% strength acetone solution, with a homogeneous solution being obtained after intensive stirring. Coating took place subsequently from solution onto a Saran-primed PET film 23 μm thick. The coatweight after drying in a drying cabinet at 120° C. was 50 g/m². The specimens were subsequently crosslinked using electron beams with an acceleration voltage of 200 kV and a dose of 40 kGy.

Polymer Blends Produced in Accordance with the Instructions:

The Polymer blending instructions were used to produce the polymer blends specified in Table 1, were the percentages are based on the mass fractions of the individual component.

TABLE 1

| Example | Component $K_c$ | Component $L_D$ | Component $L_D$ |
|---|---|---|---|
| 1 | K1 | L1, 30% | |
| 2 | K1 | L2, 30% | |
| 3 | K2, 100% | L3, 100% | |
| 4 | K1 | L4, 100% | |
| 5 | K2, 100% | L5, 100% | L1, 30% |

Results

To test the adhesives properties, PSA tape specimens were produced from Examples 1 to 5 and were subjected to adhesives testing. The results are summarized in Table 2.

TABLE 2

| Polymerblend | SST RT/(Test C) | BS-steel [N/cm]/(Test A) |
|---|---|---|
| 1 | 65 | 2.6 |
| 2 | 55 | 2.3 |
| 3 | 2520 | 2.1 |
| 4 | 385 | 2.2 |
| 5 | 4250 | 2.8 |

Application rate: 50 g/m²
SST: Shear stability times [min]
RT: Room temperature
BS: Immediate bond strength to steel The measured values demonstrate that through the inventive polymer blending of components $K_c$ and $L_D$ it is possible to obtain very different pressure-sensitive adhesives with highly variable adhesives properties.

We claim:

1. Acrylate-based pressure-sensitive adhesive comprising a polymer blend having
    (a) at least a first component $K_c$ which comprises a first acrylate block copolymer having two chemically distinguishable, covalently interlinked acrylate polymer blocks, the two polymer blocks independently of one another each being a homopolymer block of a first monomer or a copolymer block of a second monomer and a comonomer, the first monomer of the homopolymer block and the second monomer of the copolymer block being identical or different from one another, and the two polymer blocks being in microphase-separated regions and each having a softening temperature of between −125 and 19° C., and
    (b) at least one second component $L_D$, which is a second acrylate block copolymer, distinguishable from component $K_c$, having two chemically distinguishable, covalently interlinked acrylate polymer blocks, with the features specified under (a) the acrylate polymer blocks having softening temperatures of between −125 and 19° C.
    component $K_c$ and component $L_D$ both being diblock copolymers.

2. Pressure-sensitive adhesive according to claim 1, wherein the microphase-separated regions of the two distinguishable polymer blocks P of the first and the second acrylate block copolymers and the acrylate polymer $P_s$ have softening temperatures each of between −100 and 19° C.

3. Pressure-sensitive adhesive according to claim 1 or 2, wherein the at least one first component $K_c$ and the at least second component $L_D$ each have a mass fraction in the polymer blend of at least 5%.

4. Pressure-sensitive adhesive according to claim 1, wherein at least one phase of the at least one first component $K_c$ and at least one phase of the at least one second component $L_D$ are miscible with one another.

5. Pressure-sensitive adhesive according to claim 1, wherein the acrylate polymer $P_s$ of the second component $L_D$ is a homopolymer P(A) of the monomer A or a copolymer P(A/C) of the monomer A and of the comonomer C.

6. Pressure-sensitive adhesive according to claim 1, wherein the first acrylate block copolymer of the first component $K_c$ and/or the second acrylate block copolymer of the second component $L_D$ comprises a structure of the formula (I)

$$[P1_i\text{-}P2_j]_k, \tag{I}$$

in which P1 is a first polymer block of at least one first monomer and P2 is a second polymer block of at least one second monomer, the indices i and j indicating the number of the first and second polymer blocks, respectively, within the structural unit $[P1_i\text{-}P2_j]$ and k indicating the number of structural units $[P1_i\text{-}P2_j]$ within the acrylate block copolymer of formula (I), with i, j, k>0.

7. Pressure-sensitive adhesive according to claim 6, wherein in the first acrylate block copolymer of the first component $K_c$ and/or in the second acrylate block copolymer of the second component $L_D$, independently of one another, the first polymer block P1 is a polymer block P(A) of the monomer A or a copolymer block P(A/C) of the monomer A and of the comonomer C, and the second polymer block P2 is a polymer block P(B) of the monomer B or a copolymer block P(B/D) of the monomer B and of the comonomer D.

8. Pressure-sensitive adhesive according to claim 7, wherein the comonomer C of the copolymer block P(A/C) and/or the comonomer D of the copolymer block P(B/D) comprise(s) at least one functional and/or polar group that forms intermolecular interactions with another polymer macromolecule, in particular dipole-dipole interactions and/or hydrogen bonds.

9. Pressure-sensitive adhesive according to claim 7, wherein the comonomers C and D independently of one another within the copolymer block P(A/C) and P(B/D) respectively have a mass fraction of between 0.1 and 50%, in particular between 0.5 and 30%, especially between 1 and 20%.

10. Pressure-sensitive adhesive according to claim 6, wherein in that the first acrylate block copolymer of the first component $K_c$ and/or the second acrylate block copolymer of the second component $L_D$ is a diblock copolymer with i=j=k=1, comprising one polymer block P1 and one polymer block P2 in accordance with P1-P2.

11. Pressure-sensitive adhesive according to claim 10, wherein there is a mass fraction of the second polymer block P2 in the diblock copolymer P1-P2 in the range from 20 to 95%.

12. Pressure-sensitive adhesive according to claim 11, wherein the first acrylate block copolymer of the first component $K_c$ and/or the second acrylate block copolymer of the second component $L_D$ is a diblock copolymer in accordance with P(A)-P(B) or P(A)-P(B/D) or P(A/C)-P(B/D), the polymer blocks P(A) and P(B) being a polymer of the monomer A or of the monomer B respectively and the copolymer blocks P(A/C) and P(B/D) being a copolymer block of the monomers A and C or of the monomers B and D.

13. Pressure-sensitive adhesive according to claim 7, wherein the monomers A and B are selected independently of one another from the group consisting of acrylic and methacrylic monomers and, in addition, may optionally include further vinyl monomers.

14. Pressure-sensitive adhesive according to claim 13, wherein monomers A and B are of the formula (IV)

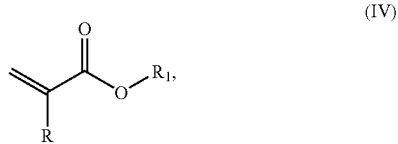

(IV)

in which R is hydrogen (H) or a methyl group and $R_1$ is a branched or unbranched, saturated $C_1$ to $C_{20}$ hydrocarbon radical.

15. Pressure-sensitive adhesive according to claim 14, wherein $R_1$ is an alkyl groupsselected from the group consisting of methyl, ethyl, n-propyl, n-butyl, n-pentyl, n-hexyl, n-heptyl, n-octyl, n-nonyl, lauryl, stearyl and its branched isomers, in particular isobutyl and isooctyl.

16. Pressure-sensitive adhesive according to claim 14, wherein $R_1$ is a bridged or unbridged, substituted or unsubstituted cycloalkyl group selected from the group consisting of cyclohexyl methacrylate, isobornyl acrylate, isobornyl methacrylate and 3,5-dimethyladamantyl acrylate.

17. Pressure-sensitive adhesive according to claim 13, wherein the vinyl monomers are selected from the group consisting of vinyl esters, vinyl ethers, vinyl halides, vinylidene halides, vinyl compounds having aromatic rings and heterocycles in α position.

18. Pressure-sensitive adhesive according to claim 17, wherein the vinyl monomers are selected from the group consisting of vinyl acetate, vinyl formamide, ethyl vinyl ether, vinyl chloride, vinylidene chloride and acrylonitrile.

19. Pressure-sensitive adhesive according to claim 5, wherein the comonomer C is selected from the group consisting of acrylic, methacrylic, acrylamide and methacrylamide monomers and vinyl monomers.

20. Pressure-sensitive adhesive according to claim 19, wherein the comonomer C carries at least one functional and/or polar group selected from the group consisting of carboxyl, sulphonic acid, phosphonic acid, hydroxyl, lactam, lactone, N-substituted amide, N-substituted amine, carbamate, epoxy, thiol, alkoxy, cyano, ether or halide group.

21. Pressure-sensitive adhesive according to claim 1, wherein the first acrylate block copolymer of the first component $K_c$ and/or the second acrylate block copolymer of the second component $L_D$ has a number average molecular weight $M_n$ of not more than 10 000 000 g/mol.

22. Pressure-sensitive adhesive according to claim 1, wherein the first acrylate block copolymer of the first component $K_c$ and/or the second acrylate block copolymer of the second component $L_D$ has a polydispersity of not more than 5.

23. Pressure-sensitive adhesive according to claim 1, wherein the first acrylate block copolymer of the first component $K_c$ and/or the second acrylate block copolymer of the second component $L_D$ has one or more grafted-on side chains.

24. Pressure-sensitive adhesive according to claim 1, further comprising tackifier resins, plasticizers, fillers, nucleators, expandants, compounding agents and/or ageing inhibitors.

25. Adhesives tapes comprising the pressure-sensitive adhesive of claim 1 applied to one or both sides of a backing material in tape form.

26. Adhesive tape according to claim 25 wherein said adhesive is applied to one or both sides of the backing material over at least part of its area.

27. Pressure-sensitive adhesive according to claim 7, wherein the comonomers C and D-are selected independently of one another from the group consisting of acrylic, methacrylic, acrylamide and methacrylamide monomers and vinyl monomers.

28. Pressure-sensitive adhesive according to claim 21, wherein the comonomers C and D carry at least one functional and/or polar group selected from the group consisting of carboxyl, sulphonic acid, phosphonic acid, hydroxyl, lactam, lactone, N-substituted amide, N-substituted amine, carbamate, epoxy, thiol, alkoxy, cyano, ether or halide group.

29. Pressure-sensitive adhesive according to any one of claims 19, 20 or 27 and 28, wherein said comonomers are of the formula (V)

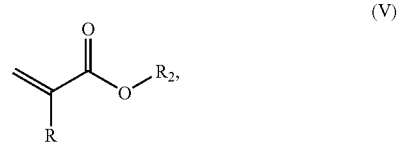

(V)

in which R is hydrogen (H) or a methyl group and $R_2$ is hydrogen (H) or a $C_1$ to $C_{30}$ hydrocarbon radical which is optionally substituted with at least one functional and/or polar group.

30. Pressure-sensitive adhesive according to any one of claims 19, 20 or 27 and 28, wherein said comonomers are selected from the group consisting of acrylic acid, methacrylic acid, hydroxyethyl acrylate, hydroxyethyl methacrylate, hydroxypropyl acrylate, hydroxypropyl methacrylate, N-methylolacrylamide, allyl alcohol, maleic an hydride, itaconic anhydride, itaconic acid, phenoxyethyl acrylate, phenoxyethyl methacrylate, 2-butoxyethyl acrylate, 2-butoxyethyl methacrylate, cyanoethyl acrylate, cyanoethyl methacrylate, 6-hydroxyhexyl methacrylate, tetrahydrofurfuryl acrylate, acrylamide and glycidyl methacrylate.

31. Pressure-sensitive adhesive according to any one of claims 19, 20 or 27 and 28, wherein said comonomers carry moderately basic functional groups selected from the group consisting of N,N-dimethylacrylamide, N,N-dimethylmethacrylamide, N-vinylpyrrolidone, N-vinyllactam, dimethylaminoethyl acrylate, dimethylaminoethyl methacrylate, diethylaminoethyl acrylate, diethylaminoethyl methacrylate, N-methylolacrylamide, N-methylolmethacrylamide, N-(butoxymethyl)methacrylamide, N-(ethoxymethyl)acrylamide and N-isopropylacrylamide.

32. Pressure-sensitive adhesive according to any one of claims 19, 20 or 27 and 28, wherein said comonomers are vinylphosphonic acid or vinylsulphonic acid.

33. Pressure-sensitive adhesive according to any one of claims 19, 20 or 27 and 28, wherein said comonomers are selected from the group consisting of N-(3-sulphopropyl)-N-acryloyloxyethyl-N,N-dimethylammonium betaine, 1-(3-sulphopropyl)-2-vinylpyridinium betaine, N-(3-sulphopropyl)-N-allyl-N,N-dimethylammonium betaine, N-(3-sulphopropyl)-N-methacryloyloxyethyl-N,N-dimethylammonium betaine and N-(3-sulphopropyl)-N-acryloyloxyethyl-N,N-dimethylammonium betaine.

34. Pressure-sensitive adhesive according to any one of claims 19, 20 or 27 and 28, wherein said comonomers are selected from the group consisting of methyl methacrylate, cyclohexyl methacrylate, t-butyl acrylate, isobornyl methacrylate, benzyl acrylate, benzoin acrylate, acrylated benzophenone, benzyl methacrylate, benzoin methacrylate, methacrylated benzophenone, phenyl acrylate, phenyl methacrylate, t-butylphenyl acrylate, t-butylphenyl methacrylate, 4-biphenylyl acrylate, 2-naphthyl acrylate and 2-naphthyl methacrylate and styrene.

35. Pressure-sensitive adhesive according to any one of claims 19, 20 or 27 and 28, wherein said comonomers are selected from the group consisting of α-methylstyrene, 4-vinylbenzoic acid, the sodium salt of 4-vinylbenzenesulphonic acid, 4-vinylbenzyl alcohol, 2-vinylnaphthalene, 4-vinylphenylboronic acid, 4-vinylpyridine, phenyl vinylsulphonate, 3,4-dimethoxystyrene, vinyl benzotrifluoride, p-methoxystyrene, 4-vinylanisole, 9-vinylanthracene, 1-vinylimidazole, 4-ethoxystyrene and N-vinylphthalimide.

36. Pressure-sensitive adhesive according to claim 8, wherein the comonomers C and D independently of one another within the copolymer block P(A/C) and P(B/D) respectively have a mass fraction of between 0.1 and 50%, in particular between 0.5 and 30%, especially between 1 and 20%.

* * * * *